United States Patent
Karppanen et al.

[11] Patent Number: 6,136,349
[45] Date of Patent: Oct. 24, 2000

[54] FOOD SEASONING, FOOD INGREDIENTS AND FOOD ITEM COMPOSITIONS AND METHODS FOR THEIR PREPARATION

[75] Inventors: Heikki Karppanen, Espoo; Pasi Heikki Karppanen, Helsinki; Pirjo Kylli Maria Laelia Karpannen, Espoo; Mari Laelia Susanna Nevalainen, Espoo; Timo Vaskonen, Helsinki, all of Finland

[73] Assignee: Pharmaconsult Oy, Espoo, Finland

[21] Appl. No.: 09/106,094

[22] Filed: Jun. 29, 1998

Related U.S. Application Data

[63] Continuation-in-part of application No. PCT/FI97/00797, Dec. 17, 1997.

[30] Foreign Application Priority Data

Dec. 30, 1996 [FI] Finland .................................... 965251

[51] Int. Cl.[7] .............................. A23L 1/22; A23L 1/304; A23D 9/007
[52] U.S. Cl. ................................. 426/2; 426/601; 426/74; 426/648; 514/171
[58] Field of Search ..................... 426/601, 602, 426/417, 2, 74, 648; 514/171

[56] References Cited

U.S. PATENT DOCUMENTS

| | | |
|---|---|---|
| 4,824,672 | 4/1989 | Day et al. . |
| 5,045,242 | 9/1991 | Roczyniak ............................. 260/424 |
| 5,158,944 | 10/1992 | Makino .................................. 514/167 |
| 5,244,887 | 9/1993 | Straub . |
| 5,502,045 | 3/1996 | Miettinen et al. . |

FOREIGN PATENT DOCUMENTS

| | | |
|---|---|---|
| 60107 | 8/1981 | Finland . |
| 2028341 | 2/1979 | United Kingdom . |
| 2266217A | 10/1993 | United Kingdom . |
| WO85/02324 | 6/1985 | WIPO . |
| WO92/19640 | 11/1992 | WIPO . |
| WO95/00158 | 1/1995 | WIPO . |
| WO95/08342 | 3/1995 | WIPO . |
| WO96/38047 | 12/1996 | WIPO . |

OTHER PUBLICATIONS

"Some Aspects of Mechanism of Inhibition of Cholesterol Absorption by β–Sitosterol" Ikuo Ikeda et al., *Biochimica et Biophysica Acta*, 732 (1983) pp. 651–658.

*Primary Examiner*—Carolyn Paden
*Attorney, Agent, or Firm*—Burns, Doane, Swecker & Mathis, LLP

[57] ABSTRACT

A method of preparing food seasoning, food ingredients and food items is disclosed, comprising the incorporation of plant sterols and/or stanols or their derivatives together with a raised level of one or more of the minerals magnesium, calcium and potassium. Ingestion of food supplied with the said combination leads to a significant decrease in both cholesterol level and blood pressure. The decrease is larger than that expected from the sum of the effects of plant sterols and minerals. Also disclosed are food seasonings for use in the preparation of foods having the said characteristics.

14 Claims, No Drawings

6,136,349

FOOD SEASONING, FOOD INGREDIENTS AND FOOD ITEM COMPOSITIONS AND METHODS FOR THEIR PREPARATION

This is a continuation-in-part U.S. application of International Application No. PCT/FI97/00797. filed Dec. 17, 1997 that designates the United States and claims priority from Finnish Application No. 965251 filed Dec. 30, 1996.

FIELD OF THE INVENTION

The present invention relates to an entirely novel principle of changing the composition of seasonings, food ingredients and food items so that oral ingestion of the ultimate edible food items results in an unexpectedly effective and lasting lowering of serum cholesterol levels. The invention enables a much better control of elevated blood pressure than could be expected on the basis of the knowledge on the effects of the use of the various ingredients according to the prior art. The present invention involves a simultaneous, appropriately high increase in the dietary concentrations of certain mineral element nutrients and those of certain natural plant sterols or their chemically modified derivatives.

BACKGROUND OF THE INVENTION

Obesity (overweight), elevated blood pressure and increased serum cholesterol levels are the main causes of cardiovascular diseases which, in turn, are the leading cause of premature deaths in all industrialized societies. In spite of enormous efforts, the average body weight of inhabitants of the industrialized societies is continuously increasing, and no effective and practical method has been found to decrease serum cholesterol and elevated blood pressure in the whole population rather than in the individuals with the highest risk only. The present invention represents a dietary method by which the above-mentioned main ailments of the industrialized societies can be practically and effectively controlled. A high serum cholesterol level is a major risk factor of coronary heart disease (also called ischaemic heart disease) which, in turn, is the leading cause of death in industrialized countries. Lowering of serum cholesterol levels decreases the incidence of coronary heart disease.

It is well-known that some plant sterols, especially beta-sitosterol and its hardened form, beta-sitostanol, decrease the absorption of dietary cholesterol from the intestine. A recent invention (PCT/FI91/00139 which corresponds to WO 92/19640) made a significant contribution to a more efficient use of the principle of the inhibition of cholesterol absorption. However, the plant sterols and stanols are able to inhibit the absorption of dietary cholesterol only if they are present in the intestine simultaneously with the dietary cholesterol. In the invention in accordance with PCT/FI91/00139, a stanol ester is incorporated in vegetable fat which is essentially free of cholesterol. Furthermore, the main embodiment of said invention is margarine which is commonly used with bread, a food item also essentially free of cholesterol. It has to be borne in mind that, by far the most prominent sources of dietary cholesterol are eggs, meats and meat products, as well as butter and other dairy products.

Moreover, the rate of the endogenous synthesis of cholesterol may be a more important factor in the long-term control of serum cholesterol level than the intestinal absorption. Unfortunately, the use of sitostanol according to PCT/FI91/00139, or increased intake of other compounds which decrease the gastrointestinal absorption of dietary cholesterol, increase the endogenous synthesis of cholesterol remarkably, by 34.9% in a recent study (T. A. Miettinen, Duodecim 1996; 112: 1149–1154). Therefore, the increased synthesis of cholesterol in the body markedly counteracts the serum cholesterol lowering effect of sitostanol and that of the natural plant sterols. These factors may explain the fact that, according to long-term experience, increased intakes of these sterols and stanols lead to a mild fall of serum cholesterol levels only. It should also be borne in mind that, the detrimental effects of a given serum cholesterol level on blood vessels and cardiovascular diseases may be remarkably influenced by several, partly hitherto unidentified factors.

SUMMARY OF THE INVENTION

It was discovered that, by increasing the levels of at least one of the essential mineral element nutrients magnesium and calcium and potassium in appropriately high concentrations in the diet and, hence, in the gastrointestinal tract simultaneously with the increase of plant sterols and/or their stanol derivatives, an unexpected beneficial interaction takes place, greatly exceeding any effect which one could expect on the basis of current knowledge. Surprisingly, the lowering of serum cholesterol levels exceeds remarkably, even several fold, that produced by the plant sterols when these agents are used according to the prior art.

An objective of the present invention was to create a method which, using naturally occurring food constituents, could produce seasoning, food ingredient and, ultimately, food compositions which, in a natural, physiological way, is able to bring about a more effective lowering of serum cholesterol than plant sterols, their stanols or the fatty acid ester derivatives of the sterols and stanols do when used according to prior art methods. In fact, a new method and compositions of food ingredient mixtures, seasonings and, ultimately, food items which, when ingested by oral route, lead to an unexpectedly effective lowering of serum cholesterol, were invented.

Another objective of the invention is to provide a food seasoning which, when used in the method according to the invention, can provide the appropriate levels of a) sterol/stanol or a fatty acid derivative thereof, b) at least one of the minerals magnesium and calcium and potassium, in the ultimate food items.

A further objective of the invention was to provide a method for lowering the serum cholesterol level and/or the blood pressure of human subjects by altering their diet to include elevated levels of a) sterol/stanol or a fatty acid derivative thereof, b) at least one of the minerals magnesium and calcium and potassium.

According to one aspect of the present invention, the levels increased are those of magnesium and calcium.

Experimental Results Demonstrating the Effectiveness of the Invention

The genetically obese Zucker rat provides a suitable model for examining the effects of various dietary factors or drugs on, among other things, serum cholesterol, and blood pressure.

The effectiveness of the present invention was studied in Zucker rats. In the beginning of the study the rats were clearly obese and had reached an average body weight of 360 grams. The serum cholesterol level was 3.0 mmol/l and the blood pressure 125 mm Hg.

Group 1 (Control diet group): During the 14-day experimental period these 10 rats received a commercial diet containing all the essential nutrients, including adequate levels of the mineral elements sodium, potassium, magnesium, and calcium, to maintain normal body functions. To mimic current human diets, the diet also comprised 18% of butter, 1% of cholesterol and sodium chloride (common salt) at the level of 6% of the dry weight of the diet.

During the following 2 weeks, the average serum cholesterol level in this group increased to the level of 10.5 mmol/l. The blood pressure increased by an average of 4 mm Hg.

Group 2 (Plant sterol diet according to the prior art): This group of 10 Zucker rats received a diet in which the caloric and other content of diet was otherwise exactly the same as in Group 1, but a mixture of the plant sterols (75% of beta-sitosterol and 25% of betasitostanol) was added to the diet at the level of 1% of the dry weight of the chow. The average serum cholesterol level was reduced by 1.6 mmol/l (15%) to the level of 8.9 mmol/l. The average rise of blood pressure was 4 mm Hg and, hence, similar to that in Group 1.

Group 3: (Diet with added calcium, magnesium and potassium): This group of 10 Zucker rats received a diet in which the caloric and other content of diet was otherwise exactly the same as in Group 1, but magnesium was added to provide an overall dietary magnesium level of 0.13%, calcium was added to provide an overall dietary calcium level of 3%, and potassium was added to provide an overall dietary potassium level of 1.57%, all based on the dry weight of the chow. These levels are higher than the existing dietary recommendations.

The serum cholesterol level was significantly lowered to an average level of 8.3 mmol/l ($p<0.05$). As compared to the cholesterol level in the control group (Group 1) the serum cholesterol level was reduced by 2.2 mmol/l (21%). There was no change in the blood pressure level.

Group 4 (Combination of the additions of plant sterols as in Group 2 and calcium, magnesium and potassium as in Group 3): This group of 10 Zucker rats received a diet in which the caloric and other content of diet was otherwise exactly the same as in Group 1, but a mixture of the plant sterols (75% of beta-sitosterol and 25% of beta-sitostanol) was added to the diet at the level of 1% of the dry weight of the chow. In addition, magnesium was added to provide an overall dietary magnesium level of 0.13%, calcium was added to provide an overall dietary calcium level of 3%, and potassium was added to provide an overall dietary potassium level of 1.57%, all based on the dry weight of the chow.

The serum cholesterol level was dramatically lowered by this diet as compared with any other of the experimental groups ($p<0.001$). In this group the average serum cholesterol level was as low as 4.6 mmol/l. Hence this diet lowered serum cholesterol as much as 5.9 mmol/l (56.2%).

Since the effect of the plant sterols in Group 1 was 1.6 mmol/l and that of the additions of calcium, magnesium, and potassium in Group 3 was 2.2 mmol/l, a larger cholesterol decrease was not to be expected than that caused by the sum of these two effects (1.6 mmol/l+2.2 mmol/l=3.8 mmol/ or 36.2%).

The actual decrease by the diet prepared according to the present innovation was, however, remarkably (2.1 mmol/l or 20%-units) more than the expected effect. Furthermore, quite unexpectedly the blood pressure was reduced by an average of 7 mm Hg, hence producing a beneficial difference of 11 mm Hg, as compared to the diet with added plant sterol (Group 2) and 7 mm Hg as compared to the diet with added calcium, magnesium and potassium. Therefore, even the beneficial effect on blood pressure was much larger than could be expected on the basis of the sum effect of added plant sterols alone, on the one hand, and added calcium, magnesium and potassium, on the other hand.

Hence, two different, important and unexpected advantages over the prior art were simultaneously produced by food prepared according to the present invention.

In the experiments described above, sodium was intentionally kept at a high level in the diet. In view of the important pathogenetic role of dietary sodium in arterial hypertension and various cardiovascular diseases it is, however, desirable to avoid excessive additions of sodium compounds. In fact, the present invention has the further advantage that it decreases the need to use salt (sodium chloride) and other sodium compounds so that, in comparison to food items in common use, a decreased sodium concentration in the ultimate edible food items is also achieved.

To examine the effects of the present invention in the obese Zucker rats further and in more detail, seasonings according to the present invention with the following contents (per cent of the total weight of the seasoning) of plant sterols, calcium (Ca), magnesium (Mg) and potassium (K) were prepared:

|  | Plant sterol | Ca | Mg | K |
| --- | --- | --- | --- | --- |
| Seasoning 1 (S1) = Example 4 | 15 | 11 | 0.65 | 8 |
| Seasoning 2 (S2) | 98 | 0.7 | 0 | 0 |
| Seasoning 3 (S3) | 2 | 0 | 10 | 25 |

To produce fat spreads according to the invention, each of these seasonings was mixed with butter which had the following contents (per cent of the total weight of the butter) of plant sterols, calcium (Ca), magnesium (Mg) and potassium (K):

|  | Plant sterol | Ca | Mg | K |
| --- | --- | --- | --- | --- |
| Butter | 0.2 | 0 | 0 | 0 |

The final fat spread comprised 15% of the seasoning and 85% of butter. Seasoning 1, 2, and 3 produced the following compositions in Fat spread 1, 2 and 3, respectively:

|  | Plant sterol | Ca | Mg | K |
| --- | --- | --- | --- | --- |
| Fat spread 1 | 2.3 | 1.65 | 0.0975 | 1.2 |
| Fat spread 2 | 15 | 0.1 | 0 | 0 |
| Fat spread 3 | 0.5 | 0 | 1.5 | 3.75 |

In addition, another fat spread, representing the composition given in the example and having the following composition, was prepared:

|  | Plant sterol | Ca | Mg | K |
| --- | --- | --- | --- | --- |
| Fat spread 4 | 15 | 0.044 | 0.024 | 0.29 |

For the studies, a white bread with the following contents (per cent of the total weight of the bread) of plant sterols, calcium (Ca), magnesium (Mg) and potassium (K) was prepared:

|  | Plant sterol | Ca | Mg | K |
|---|---|---|---|---|
| Bread 1 (=Basic) | 0.04 | 0.01 | 0.01 | 0.1 |

The function of the invention was examined by preparing the diets in the following way: Each of the diets comprised 81% of the basic bread (see above) and 1% of cholesterol. One of the diets contained 18% butter. This control diet had the following contents (per cent of the total weight of the bread) of plant sterols, calcium (Ca), magnesium (Mg) and potassium (K):

| Plant sterol | Ca | Mg | K |
|---|---|---|---|
| 0.066 | 0.008 | 0.008 | 0.081 |

The diets according to the present invention contained 18% of the fat spreads 1, 2, 3 and 4. Hence, the concentrations of plant sterols, calcium, magnesium, and potassium in the diets were as follows, respectively (percent of the dry weight):

|  | Plant sterol | Ca | Mg | K |
|---|---|---|---|---|
| Diet 1 | 0.375 | 0.255 | 0.0226 | 0.261 |
| Diet 2 | 2.73 | 0.026 | 0.008 | 0.081 |
| Diet 3 | 0.12 | 0.008 | 0.278 | 0.756 |
| Diet 4 | 2.73 | 0.016 | 0.012 | 0.133 |

The serum cholesterol level was measured in groups of 8 rats receiving each of the diets for 14 days. In the group receiving the control diet the serum cholesterol level was 9.5 mmol/l. Diet 1 according to the invention lowered the serum cholesterol level by 18.6%. In the group receiving otherwise exactly the same diet without the increased levels of plant sterols, the decrease in cholesterol level was 4.8%, and in a group receiving otherwise exactly the same diet containing the increased levels of plant sterols but without the increased levels of the mineral elements Ca, Mg and K the decrease in cholesterol level was 3.8%.

Diet 2 according to the invention lowered the serum cholesterol level by 22.3%.

In the group receiving otherwise exactly the same diet without the increased levels of plant sterols, the decrease in cholesterol level was 1.8%, and in a group receiving otherwise exactly the same diet containing the increased levels of plant sterols but without the increased levels of the mineral elements Ca, Mg and K, the decrease in cholesterol level was 12.3%.

Diet 3 according to the invention lowered the serum cholesterol level by 12.5%. In the group receiving otherwise exactly the same diet without the increased levels of plant sterols, the decrease in cholesterol level was 4.4%, and in a group receiving otherwise exactly the same diet containing the increased levels of plant sterols but without the increased levels of the mineral elements Ca, Mg and K the decrease in cholesterol level was 0.8%.

Diet 4 according to the invention lowered the serum cholesterol level by 21.3%. In the group receiving otherwise exactly the same diet without the increased levels of plant sterols, the decrease in cholesterol level was 2.5%, and in a group receiving otherwise exactly the same diet containing the increased levels of plant sterols but without the increased levels of the mineral elements Ca, Mg and K the decrease in cholesterol level was 12.7%

For another set of experiments a white bread with the following contents (per cent of the total weight of the bread) of plant sterols, calcium (Ca), magnesium (Mg) and potassium (K) as prepared:

|  | Plant sterol | Ca | Mg | K |
|---|---|---|---|---|
| Bread 1 (=Basic) | 0.04 | 0.01 | 0.01 | 0.1 |

In addition, butter with the following contents (per cent of the total weight of the butter) of plant sterols, calcium (Ca), magnesium (Mg) and potassium (K) was used:

|  | Plant sterol | Ca | Mg | K |
|---|---|---|---|---|
| Butter | 0.2 | 0 | 0 | 0 |

The function of the invention was examined by preparing the diets in the following way: Each of the diets contained 18% butter and 1% of cholesterol. One of the diets contained 81% of the basic bread (see above). This control diet had the following contents (per cent of the total weight of the bread) of plant sterols, calcium (Ca), magnesium (Mg) and potassium (K):

| Plant sterol | Ca | Mg | K |
|---|---|---|---|
| 0.066 | 0.008 | 0.008 | 0.081 |

Three other breads (breads 2, 3 and 4) had the following contents (per cent of the total weight of the bread) of plant sterols, calcium (Ca), magnesium (Mg) and potassium (K):

|  | Plant sterol | Ca | Mg | K |
|---|---|---|---|---|
| Bread 2 | 8 | 0.01 | 1 | 1.5 |
| Bread 3 | 0.1 | 1 | 0.01 | 0.1 |
| Bread 4 (=Example) | 2.9 | 0.046 | 0.03 | 0.22 |

Diet 5 (containing bread 2), diet 6 (containing bread 3), and diet 7 (containing bread 4) according to the present invention contained 81% of the breads 2, 3 and 4. Hence, the concentrations of plant sterols, calcium, magnesium, and potassium in the diets were as follows, respectively:

|  | Plant sterol | Ca | Mg | K |
|---|---|---|---|---|
| Diet 5 | 6.516 | 0.008 | 0.81 | 1.215 |
| Diet 6 | 0.116 | 0.81 | 0.0081 | 0.081 |
| Diet 7 | 2.385 | 0.037 | 0.024 | 0.0396 |

The serum cholesterol level was measured in groups of 6 rats receiving each of the diets for 7 days. In the group receiving the control diet the serum cholesterol level was 10.4 mmol/l.

Diet 5 according to the invention lowered the serum cholesterol level by 51.6%.

In the group receiving otherwise exactly the same diet without the increased levels of plant sterols, the decrease in cholesterol level was 8.6%, and in a group receiving otherwise exactly the same diet containing the increased levels of plant sterols but without the increased levels of the mineral elements Ca, Mg and K the decrease in cholesterol level was 16.3%.

Diet 6 according to the invention lowered the serum cholesterol level by 15.6% In the group receiving otherwise exactly the same diet without the increased levels of plant sterols, the decrease in cholesterol level was 7.6%, and in a group receiving otherwise exactly the same diet containing the increased levels of plant sterols but without the increased levels of the mineral elements Ca, Mg and K, the decrease in cholesterol level was 1.1%.

Diet 7 according to the invention lowered the serum cholesterol level by 27.4% In the group receiving otherwise exactly the same diet without the increased levels of plant sterols, the decrease in cholesterol level was 6.6%, and in a group receiving otherwise exactly the same diet containing the increased levels of plant sterols but without the increased levels of the mineral elements Ca, Mg and K the decrease in cholesterol level was 10.3%.

Based on the above results, concentration values for human total daily diets according to this invention may be calculated, containing per dry weight of the diet Plant sterols 0.12 to 6.5%
Calcium 0.15 to 3%
Magnesium 0.08 to 0.8%
Potassium 0.4 to 1.6%

DESCRIPTION OF THE PREFERRED EMBODIMENTS

As the source of beta-sitosterol, beta-sitostanol, stigmasterol, stigmastanol, campesterol, campestanol, dihydrobrassicasterol, and dihydrobrassicastanol, said sterols and stanols hereinafter referred to as "plant sterol/stanol", it is possible to use in the method according to the present invention:

1) Naturally occurring plant sterols and stanols, particularly beta-sitosterol and betasitostanol but also stigmasterol, campesterol, and dihydrobrassicasterol concentrated or purified from tall oil, soy beans, rapeseeds, coconuts, corn, peanuts, or other natural sources. Methods previously published and generally known to those skilled in the art are applied to improve the solubility of "plant sterol/stanol" while incorporating these compounds in food ingredients, seasonings and food items according to the present invention. When plant concentrates with high concentrations of sterols are used, there is no need to remove such naturally occurring, accompanying compounds as phytoestrogens and flavonoids which, when left in the sterol concentrate, may even further enhance the beneficial health effects of the ultimate edible food items prepared according to the present invention. In fact, the present invention could serve as a suitable vehicle for supplementation of phytoestrogens, flavonoids, beta-carotene, vitamins A, D, and E as well as other vitamins, other mineral elements and other beneficial dietary factors, other active ingredients of natural origin, or even drugs.

2) It is also possible to use the hydrogenated forms of the aforementioned natural plant sterols, the so-called stanols.

3) Both the sterols and stanols can be used either as the unmodified parent compounds, or as their fatty acid esters if a good solubility in the fatty part of the food ingredients, seasoning mixtures, or the ultimate edible food items is desired.

As the source of the mineral element nutrient cations, in the method according to the present invention it is possible to use any physiologically acceptable magnesium, calcium or potassium compound.

Preferable magnesium compounds include, but are not limited to, in particular magnesium sulphate, magnesium chloride, magnesium hydroxide, magnesium oxide, and magnesium carbonate, but also many other compounds such as magnesium salts of amino acids and other physiologically acceptable magnesium compounds are possible.

Preferable calcium compounds include, but are not limited to, in particular calcium carbonate, calcium lactate, and calcium chloride, but also many other compounds such as calcium phosphates, calcium sulphate, calcium citrates, calcium tartrate, calcium acetate, calcium propionate, calcium alginate, calcium glutamate, calcium gluconate and other physiologically acceptable calcium compounds are possible.

Preferable potassium compounds include, but are not limited to, in particular potassium chloride, potassium(bi)carbonate, potassium lactate, and potassium sulphates, but also many other potassium compounds such as potassium phosphates, potassium tartrate, potassium acetate, potassium propionate, potassium alginate, potassium gluconate, potassium-rich dietary fibers, and other physiologically acceptable potassium compounds are possible.

The method in accordance with the present invention can be used for changing the composition of a number of food items, such as, for example, bread, cookies and biscuit-like products; sausages and other meat products; egg foods, dairy products, baby foods, salad dressings, and also for novel seasoning compositions. Seasoning compositions according to the present invention can be used for the seasoning of, for example, such food items as bacon, eggs, miso and other soups, porridge meals, corn flakes, rice flakes, rice cakes, wheat flakes, oat flakes, rye flakes, barley flakes, and various types of "muesli". These may be prepared and seasoned according to conventional industrial practices, except that a part or all of the conventional seasonings and salt are replaced by the above described seasoning. In most instances the conventional use of common salt can be entirely avoided by the use of the seasonings prepared according to the present invention.

Seasonings according to the present invention can also be used to replace common salt in a great variety of other industrially prepared food items as well as in the preparation of foods both in restaurants, catering, home kitchens etc. Such seasonings are particularly suitable for soups, beefs and other foods in which salty and/or spicy seasonings are used, for the preparation of various food ingredient mixtures, such as, for example, flour or meal and salt mixtures for the preparation of bread, muesli, corn and rice flakes and breakfast cereal products. These ingredient mixtures and seasonings, when added to various foods, change the food composition in accordance with the method of the present invention.

In the following, examples are given to demonstrate the preparation of food seasoning and food items according to the present invention. In these examples, "plant sterol/stanol" refers to the combined weight of beta-sitosterol, beta-sitostanol, stigmasterol, stigmastanol, campesterol, campestanol, dihydrobrassicasterol, and dihydrobrassicastanol, represented by the parent compound only, i.e., excluding the weight of the possible fatty acids esterified to the sterols and stanols.

EXAMPLE 1
White Bread

A pre-mix is made of the following formulation:

| | |
|---|---|
| Sodium chloride | 0.60 kg |
| "Plant sterol/stanol" | 2.00 kg |
| Magnesium sulphate (MgSO$_4$ · 7H$_2$O) | 0.126 kg |
| Magnesium hydroxide {Mg(OH)$_2$} | 0.020 kg |
| Calcium carbonate | 0.080 kg |
| Potassium chloride | 0.294 kg |
| 1-lysine hydrochloride | 0.021 kg |
| Wheat flour | 7.500 kg |

The following ingredients are added to the pre-mix, and a conventional white bread is made in a conventional commercial baking operation by the straight dough method:

| | |
|---|---|
| Wheat flour | 30.00 kg |
| Vital wheat gluten | 0.37 kg |
| Promosoy 13[1] | 0.55 kg |
| Format[2] | 0.50 kg |
| Shortening (vegetable oil) | 1.12 kg |
| Yeast | 1.75 kg |
| Water | 23.75 kg |

[1]Contains soy protein isolate, non-fat dry milk and emulgators (Engelhardt & Co., Sweden)
[2]Contains diacetyl tartaric acid esters, CaCO$_3$ and ascorbic acid with malt flour and sugar (Ireks Arkady, Germany)

The formulation, containing all the ingredients, is mixed at low speed, dough temperature 27° C., floor time 30 min, baked in the form of Pullman loaves, fermentation ca. 40 min at 38–40° C. and 80% relative humidity, baked for 30 min at an oven temperature of 230° C. This is a good, commercial quality, standard white bread.

EXAMPLE 2
Rye Bread

A pre-mix is made of the following formulation:

| | |
|---|---|
| Sodium chloride | 0.60 kg |
| "Plant sterol/stanol" | 2.00 kg |
| Magnesium sulphate (MgSO$_4$.7H$_2$O) | 0.126 kg |
| Magnesium hydroxide {Mg(OH)$_2$} | 0.020 kg |
| Calcium carbonate | 0.080 kg |
| Potassium chloride | 0.294 kg |
| 1-lysine hydrochloride | 0.021 kg |
| Rye meal[1] | 9.57 kg |

The following ingredients are added to the pre-mix, and a conventional sour rye bread is made in a conventional commercial baking operation:

| | |
|---|---|
| Rye meal[1] | 20.00 kg |
| Vital wheat gluten | 0.64 kg |
| Coarse rye meal | 5.71 kg |
| Wheat flour | 10.00 kg |
| Yeast | 0.67 kg |
| Water | 33.37 kg |

[1]Part of rye meal and water are fermented with natural starter overnight, final pH 3.9.

The formulation, containing all the ingredients, is mixed for 7 min at low speed, dough temperature 27° C., dough pH 4.4, floor time 60 min, baked in the form of Pullman loaves, ferntation ca. 40 min at 38–40° C. and 70% relative humidity, baked for 37 min at an oven temperature of 230° C. This is a good, commercial quality, standard sour rye bread. Preferably, the concentrations by weight of plant stero/stanol or derivatives thereof, and of The advantageous mineral elements in the final bread products made by the method according to the present invention are: Sterol 0.1–8%, Mg 0.01–1%, Ca 0.01–1%, and K 1–1.5%. More preferably, said concentrations are in the ranges: Sterol 0.5–5%, Mg 01–0.06%, Ca 0.02–0.08%, and K 0.05–0.4%.

EXAMPLE 3
Marinade

A marinade for various types of meats, fish and vegetables is made in a conventional commercial operation from the following formulation:

| | |
|---|---|
| Vegetable oil | 0.7680 kg |
| "Plant sterol/stanol" | 0.1440 kg |
| Calcium chloride (CaCl$_2$.6H$_2$O) | 0.0023 kg |
| Magnesium sulphate (MgSO$_4$.7H$_2$O) | 0.0023 kg |
| Potassium chloride (KCl) | 0.0054 kg |
| Sodium chloride (NaCl) | 0.0109 kg |
| 1-Lysine hydrochloride | 0.0004 kg |
| Honey | 0.0288 kg |
| Vinegar (10 weight %) | 0.0288 kg |
| Spices | 0.0096 kg |

The "Plant sterol/stanol" is first mixed with the vegetable oil. Calcium chloride, magnesium sulphate, potassium chloride, sodium chloride, 1-lysine hydrochloride and honey are mixed with vinegar, and the mixture and the spices are added to the mixture of the vegetable oil and "Plant sterol/stanol". All the ingredients are mixed thoroughly. Preferably, the concentrations by weight of plant sterol/stanol or derivatives thereof, and of the advantageous mineral elements in the marinades made by the method according to the present invention are: Sterol 0.5–18%, Mg 0–1%, Ca 0–1%, and K 0–2.5%. More preferably, said concentrations are in the ranges: Sterol 5–15%, Mg 0.01–0.04%, Ca 0.02–0.06%, and K 0.01–0.6%.

EXAMPLE 4
Seasoning 4

A mechanical mixture of the following formulation is made:

| | |
|---|---|
| "Plant sterol/stanol" | 2.12 kg |
| Calcium carbonate (CaCO$_3$) | 3.80 kg |
| Magnesium sulphate (MgSO$_4$.7H$_2$O) | 0.910 kg |
| Potassium chloride (KCl) | 2.12 kg |
| Sodium chloride (NaCl) | 4.32 kg |
| Sodium glutamate | 0.40 kg |
| 1-Lysine hydrochloride | 0.15 kg |
| (Spices; optional) | 1.00 kg |

All the ingredients are mixed thoroughly with a conventional industrial mixer but taking care that excessive heat is not formed during the process. Preferably, the concentrations by weight of plant sterol/stanol or derivatives thereof, and of the advantageous mineral elements in the final seasoning made by the method according to the present invention are: Sterol 2–98%, Mg 0–30%, Ca 0–30%, and K 0–50%. More preferably, said concentrations are in the ranges: Sterol 10–20%, Mg 0.2–1%, Ca 5–15%, and K 1–12%.

EXAMPLE 5

Sausage

A pre-mix of the following formulation is made:

| | |
|---|---|
| "Plant sterol/stanol" | 0.270 kg |
| Calcium chloride (CaCl$_2$.6H$_2$O) | 0.057 kg |
| Magnesium sulphate (MgSO$_4$.7H$_2$O) | 0.057 kg |
| Potassium chloride (KCl) | 0.132 kg |
| Potassium lactate | 0.090 kg |
| Sodium chloride (NaCl) | 0.270 kg |
| Sodium lactate | 0.090 kg |
| l-Lysine hydrochloride | 0.010 kg |

This pre-mix is thoroughly mixed with the following ingredients:

| | |
|---|---|
| Meat, including natural fat | 12.500 kg |
| Milk powder | 0.840 kg |
| Potatoe starch | 1.160 kg |
| Water | 6.450 kg |
| Sodium nitrite (NaNO$_2$, 10% solution) | 0.030 kg |
| Spices | 0.085 kg |

The sausage is processed according to generally known conventional industrial techniques.

EXAMPLE 6

Mincemeat Steak (Hamburger Steak)

| | |
|---|---|
| Minced meat | 9.67 kg |
| "Plant sterol/stanol" | 0.07 kg |
| Seasoning of example 4 (with spices) | 0.26 kg |

The plant sterol and the seasoning are mixed with the minced meat. Thereafter the mincemeat steak is prepared according to the processes conventionally used in the preparation of steaks, e.g for hamburger restaurants. One serving is a 200 gram steak.

EXAMPLE 7

Steak of Minced Fish

| | |
|---|---|
| Minced fish | 9.67 kg |
| "Plant sterol/stanol" | 0.07 kg |
| Seasoning of example 4 (with spices) | 0.26 kg |

The plant sterol and the seasoning are mixed with the minced fish. Thereafter the steak of minced fish is prepared according to the processes conventionally used in the preparation of steaks for hamburger restaurants. One serving is a 200 gram steak.

EXAMPLE 8

Soy Steak

| | |
|---|---|
| Soy protein mixture | 9.67 kg |
| "Plant sterol/stanol" | 0.07 kg |
| Seasoning of example 4 (with spices) | 0.26 kg |

The plant sterol and the seasoning are mixed with the soy protein mixture conventionally used for the preparation of soy steaks. Thereafter the steak is prepared according to the processes conventionally used in the preparation of soy steaks. One serving is a 200 gram steak.

Preferably, the concentrations by weight of plant sterol/stanol or derivatives thereof, and of the advantageous mineral elements in the final sausage or steak products made by the method according to the present invention are: Sterol 0.1–10%, Mg 0.01–1.5%, Ca 0.01–1.5%, and K 0.114 1.5%. More preferably, said concentrations are in the ranges: Sterol 0.5–2%, Mg 0.01–0.03%, Ca 0.01–0.5%, and K 0.1–0.8%.

EXAMPLE 9

Mayonnaise

| | |
|---|---|
| Vegetable oil | 0.650 kg |
| "Plant sterol/stanol" | 0.065 kg |
| Calcium chloride (CaCl$_2$.6H$_2$O) | 0.0012 kg |
| Magnesium sulphate (MgSO$_4$.7H$_2$O) | 0.0012 kg |
| Potassium chloride (KCl) | 0.0028 kg |
| Sodium chloride (NaCl) | 0.0057 kg |
| l-Lysine hydrochloride | 0.0002 kg |
| Sugar | 0.030 kg |
| Vinegar (10 weight %) | 0.030 kg |
| Mustard | 0.020 kg |
| Water | 0.194 kg |

The mayonnaise is prepared by homogenization by conventional industrial methods. Preferably, the concentrations by weight of plant sterol/stanol or derivatives thereof, and of the advantageous mineral elements in the final mayonnaise made by the method according to the present invention are: Sterol 0.5–15%, Mg 0–3%, Ca 0–3%, and K 0–3%. More preferably, said concentrations are in the ranges: Sterol 2–12%, Mg 0.005–0.025%, Ca 0.01–0.04%, and K 0.01–0.3%.

EXAMPLE 10

Mixture of Vegetable Oil and Butter

| | |
|---|---|
| Vegetable oil | 0.350 kg |
| "Plant sterol/stanol" | 0.150 kg |
| Butter | 0.478 kg |
| Calcium chloride (CaCl$_2$.6H$_2$O) | 0.0024 kg |
| Magnesium sulphate (MgSO$_4$.7H$_2$O) | 0.0024 kg |
| Potassium chloride (KCl) | 0.0056 kg |
| Sodium chloride (NaCl) | 0.0114 kg |
| l-Lysine hydrochloride | 0.0004 kg |

The plant sterol is added to the vegetable oil and mixed thoroughly. Thereafter this mixture and the other ingredients are added to the butter and mixed according to conventional dairy practice to make the mixture of vegetable oil and butter. Preferably, the concentrations by weight of plant sterol/stanol or derivatives thereof, and of the advantageous mineral elements in the final vegetable oil/butter products made by the method according to the present invention are: Sterol 0.5–15%, Mg 0–0.4%, Ca 0.1–1%, and K 0–1.5%. More preferably, said concentrations are in the ranges: Sterol 5–15%, Mg 0.01–0.04%, Ca 0.02–0.06%, and K 0.1–0.5%.

EXAMPLE 11

Salad Dressing

| | |
|---|---|
| Vegetable oil | 2.0000 kg |
| "Plant sterol/stanol" | 0.2000 kg |
| Calcium chloride (CaCl$_2$.6H$_2$O) | 0.0048 kg |
| Magnesium sulphate (MgSO$_4$.7H$_2$O) | 0.0048 kg |

-continued

| | |
|---|---|
| Potassium chloride (KCl) | 0.0112 kg |
| Sodium chloride (NaCl) | 0.0228 kg |
| 1-Lysine hydrochloride | 0.0008 kg |
| Vinegar (10 weight %) | 0.1200 kg |
| Water | 1.6360 kg |

The salad dressing is prepared by homogenization by conventional industrial methods. Preferably, the concentrations by weight of plant sterol/stanol or derivatives thereof, and of the advantageous mineral elements in the final salad dressing made by the method according to the present invention are: Sterol 0.5–8%, Mg 0–3%, Ca 0–3%, and K 0–3%. More preferably, said concentrations are in the ranges: Sterol 0.5–8%, Mg 0.005–0.025%, Ca 0.01–0.04%, and K 0.05–0.30%.

EXAMPLE 12

Yogurt

During the preparation of 100 kg of yogurt according to conventional commercial techniques the following ingredients are added and carefully mixed:

| | |
|---|---|
| "Plant sterol/stanol" | 1.000 kg |
| Magnesium oxide (MgO) | 0.225 kg |

Preferably, the concentrations by weight of plant sterol/stanol or derivatives thereof, and of the advantageous mineral elements in the final yogurt made by the method according to the present invention are: Sterol 0.2–10%, Mg 0.01–3%, Ca 0.1–3%, and K 0.1–3%. More preferably, said sterol and magnesium concentrations are in the ranges: Sterol 0.5–2% and Mg 0.05–0.3%

What we claim is:

1. A method of treating a food seasoning, good ingredient or food composition such that upon ingestion it results in a decrease in serum cholesterol and blood pressure relative to an otherwise identical, untreated food seasoning, food ingredient, or food composition, wherein said treatment consists essentially of adding to said food seasoning, food ingredient, or food composition at least one material that provides for an increase in the amount of plant sterol/stanol, wherein said material is selected from the group consisting of beta-sitosterol, stigmasterol, campesterol, dihydrobrassicasterol, hardened stanol forms of said sterols, and fatty acids of said sterols and stanols, and at least one material that provides for an increase in a mineral nutrient selected from the group consisting of magnesium, calcium and potassium, and wherein the combined amounts of said material that provides for increased sterol/stanol and said material that provides for an increase in said mineral are sufficient to result in greater serum cholesterol and blood pressure lowering activity when ingested than the additive effect of either material if utilized singularly.

2. A method according to claim 1, wherein the plant sterol/stanol has been concentrated or purified from a natural plant sterol source.

3. A method according to claim 2, wherein said plant sterol/stanol comprises beta-sitosterol, beta-sitostanol or a mixture thereof.

4. A method according to claim 1, comprising incorporating in said composition at least one plant sterol/stanol so as to produce an increase of 1% or more of plant sterol/stanol in the dry weight of the diet.

5. A method according to claim 1, wherein increased levels of magnesium and calcium are provided in said composition.

6. A method according to claim 5, wherein additionally an increased level of potassium is provided in said composition.

7. A method according to claim 1, wherein an increased level of magnesium is provided by incorporating in said composition a magnesium compound selected from the group consisting of magnesium sulphate, magnesium chloride, magnesium hydroxide, magnesium oxide, magnesium carbonate, amino acid magnesium salts and mixtures thereof.

8. A method according to claim 1, wherein an increased level of calcium is provided by incorporating in said composition a calcium compound selected from the group consisting of calcium phosphates, calcium carbonate, calcium sulphate, calcium chloride, calcium lactate, calcium citrates, calcium acetate, calcium propionate, calcium tartrate, calcium alginate, calcium gluconate, calcium glutamate and mixtures thereof.

9. A method according to claim 1, wherein an increased level of potassium is provided by incorporating in said composition a potassium compound selected from the group consisting of potassium phosphates, potassium carbonate, potassium bicarbonate, potassium sulphate, potassium chloride, potassium lactate, potassium acetate, potassium propionate, potassium tartrate, potassium alginate, potassium gluconate and mixtures thereof.

10. A method according to claim 1, comprising providing in said composition a decreased level of sodium chloride.

11. A method according to claim 1, wherein the resulting concentration of plant sterol/stanol in the diet is in the range about 0.12 to 6.5 per cent, the concentration of calcium in the diet is in the range about 0.15 to 3 per cent, the concentration of magnesium in the diet is in the range about 0.08 to 0.8 per cent and the concentration of potassium in the diet is in the range about 0.4 to 1.6 per cent, all calculated on the dry weight of the diet.

12. The method of claim 1, wherein said food seasoning, ingredient or composition provides for serum cholesterol to be reduced and blood pressure to be lowered in a subject without reducing the average amount of cholesterol that is consumed by said subject.

13. A treated food seasoning, food ingredient, or food composition which, upon ingestion, results in a decrease in serum cholesterol and blood pressure relative to an otherwise identical but untreated food seasoning, ingredient, or composition, wherein said treatment consists essentially of adding to a food seasoning, food ingredient, or food composition that is to be ingested, at least one material that provides for an increase in the amount of plant sterol/stanol, wherein said material is selected from the group consisting of beta-sitosterol, stigmasterol, campesterol, dihydrobrassicasterol, hardened stanol forms of said sterols, and fatty acids of said sterols and stanols, and at least one material that provides for an increase in a mineral nutrient selected from the group consisting of magnesium, calcium and potassium, and wherein the combined amounts of said material which provides for increased sterol/stanol and said material and which provides for an increase in said mineral are sufficient to result in greater serum cholesterol and blood pressure lowering activity than the additive effect of either material if utilized singularly.

14. A method of lowering serum cholesterol levels and/or elevated blood pressure by administering to a subject a diet comprising at least one food seasoning, food ingredient and/or food composition according to claim 13.

* * * * *

UNITED STATES PATENT AND TRADEMARK OFFICE
CERTIFICATE OF CORRECTION

PATENT NO. : 6,136,349
DATED : October 24, 2000
INVENTOR(S) : Heikki Karppanen et al.

It is certified that error appears in the above-identified patent and that said Letters Patent is hereby corrected as shown below:

Column 13,
Line 36, delete "good" and insert -- food --
Line 47, delete "acids" and insert -- acid esters --.

Column 14,
Line 53, delete "acids" and insert -- acid esters --.

Signed and Sealed this

Second Day of July, 2002

Attest:

JAMES E. ROGAN
Attesting Officer    Director of the United States Patent and Trademark Office

US006136349C1

(12) EX PARTE REEXAMINATION CERTIFICATE (7928th)

United States Patent
Karppanen et al.

(10) Number: US 6,136,349 C1
(45) Certificate Issued: Dec. 14, 2010

(54) FOOD SEASONING, FOOD INGREDIENTS AND FOOD ITEM COMPOSITIONS AND METHODS FOR THEIR PREPARATION

(75) Inventors: Heikki Karppanen, Espoo (FI); Pasi Heikki Karppanen, Helsinki (FI); Pirjo Kylli Maria Laelia Karpannen, Espoo (FI); Mari Laelia Susanna Nevalainen, Espoo (FI); Timo Vaskonen, Helsinki (FI)

(73) Assignee: Multibene Ingredients Oy Ltd., Espoo (FI)

Reexamination Request:
No. 90/009,487, Jul. 16, 2009

Reexamination Certificate for:
Patent No.: 6,136,349
Issued: Oct. 24, 2000
Appl. No.: 09/106,094
Filed: Jun. 29, 1998

Certificate of Correction issued Jul. 2, 2002.

Related U.S. Application Data

(63) Continuation-in-part of application No. PCT/FI97/00797, filed on Dec. 17, 1997.

(30) Foreign Application Priority Data

Dec. 30, 1996 (FI) .................................................. 965251

(51) Int. Cl.
A23L 1/30 (2006.01)
A23L 1/22 (2006.01)
A23L 1/24 (2006.01)
A23L 1/314 (2006.01)
A23L 1/304 (2006.01)
A21D 2/36 (2006.01)
A21D 13/08 (2006.01)
A23C 9/123 (2006.01)
A23D 7/00 (2006.01)
A23D 9/00 (2006.01)
A61K 31/575 (2006.01)
A61K 33/06 (2006.01)

(52) U.S. Cl. ............................ 426/2; 426/601; 426/648; 426/74; 514/171

(58) Field of Classification Search ........................ None
See application file for complete search history.

(56) References Cited

U.S. PATENT DOCUMENTS 3,004,043 A 10/1961 Stern
4,160,850 A 7/1979 Hallstrom et al.
4,588,717 A 5/1986 Mitchell
4,797,289 A 1/1989 Reddy
4,883,788 A 11/1989 Day et al.
5,545,414 A 8/1996 Behr et al.

FOREIGN PATENT DOCUMENTS

EP 377119 A1 7/1990
EP 594612 B1 11/1992
EP 839458 A1 5/1998
JP 57-018617 1/1982
JP 58-116415 11/1983
JP 01-300874 5/1989
JP 02-265456 10/1990
JP 04-036158 6/1992
JP 08-301770 11/1996
SU 414989 A1 9/1974
WO 9638047 A1 12/1996
WO 9819556 A1 5/1998

OTHER PUBLICATIONS

USDA National Nutrient Database for Standard Reference, Release 17; Calciuum Content of Selected Foods per Common measure, [online] [retrieved Nov. 4, 2009], http://www.nal.usda.gov/fnic/foodcomp/Data/SR17/wtrank/sr17w301.pdf ("USDA I").*

USDA National Nutrient Database for Standard Reference, Release 17; Potassium Conntent of Selected Foods per Common measure, [online] [retrieved Nov. 4, 2009], http://www.nal.usda.gov/fnic/foodcomp/Data/SR17/wtrank/sr17a306.pdf ("USDA II").*

USDA National Nutrient Database for Standard Reference, Release 17; Magnesium Conntent of Selected Foods per Common measure, [online] [retrieved Nov. 4, 2009], http://www.nal.usda.gov/fnic/foodcomp/Data/SR17/wtrank/sr17a304.pdf ("USDA III").*

Foschi, M. and U. Arena (1990) Clin. Ter. 135(2):115–120 Abstract Only.

Capurso, A. et al. (1999) Aging (Milano) 11(4):273–276 Abstract Only.

Karppanen H (1994) Journal of the American College of Nutrition, 13(5):493–5.

Sarkkinen E et al. (1999) Study Report, "Efect of low fat and low salted meat products enriched with MultiBene on serum total, lipoprotein lipids and blood pressure in subjects with mild to moderate hypercholesterolemia".

Pomeranze J. et al. (1960) American Journal of Clinical Nutrution 8:340–4.

Tikkanen, M. et al. (2001) Am. J. Cardiol. 88: 1157–1162.

Pelletier, X. et al. (1995) Ann. Nutr. Metab. 39:291–295 (1995).

Law, M. (2000) British Medical Journal 320:861–864.

Gylling, H. et al. (2001) Curr Control Trials Cardiovasc Med. 2(3):123–128.

Weihrauch, J. et al. (1978) J. Am. Dietetic Assoc. 73:39–49.

(Continued)

*Primary Examiner*—Bruce Campell

(57) ABSTRACT

A method of preparing food seasoning, food ingredients and food items is disclosed, comprising the incorporation of plant sterols and/or stanols or their derivatives together with a raised level of one or more of the minerals magnesium, calcium and potassium. Ingestion of food supplied with the said combination leads to a significant decrease in both cholesterol level and blood pressure. The decrease is larger than that expected from the sum of the effects of plant sterols and minerals. Also disclosed are food seasonings for use in the preparation of foods having the said characteristics.

OTHER PUBLICATIONS

Mervaala, E. (1995) "A Potassium–, Magnesium– and L–Lysine Enriched Mineral Salt" Graduate Dissertation, Institute of Biomedicine Department of Pharmacology and Toxicology, University of Helsinki, Finland.
Vaskonene, T. (2002) "Dietary Combination of Mineral Nutrients and Natural Plant Sterols" Graduate Dissertation, Institute of Biomedicine Department of Pharmacology, University of Helsinki, Finland.
Nicolosi, R. et al. (1991) Artherosclerosis 88:133–142.
Seetharamaiah, G. and N. Chandrasekhara (1989) Artherosclerosis 78:219–223.
Gunstone, F. et al. "The Lipid Handbook" (2 ed. 1994), p. 125.
European Commission, Scientific Committee of Food "Opinion of the Scientific Committee on Food on an application from MultiBene for approval of plant–sterol enriched foods" Apr. 15, 2003.
Vaskonen, T. et al. (2001) Nutr. Metab. Cardiovase Dis. 11:158–167.
Singh, R. et al. (1991) Biological Trace Element Research 30:59–64.
Patki, P. et al. (1990) British Medical Journal 301:521–523.
Feldman, E. et al. (1987) Journal American College of Nutrition 6(6):475–484.
Castelli, P. and K. Anderson (1986) American Journal of Medicine 80(supp. 2a):23–32.
Anderson, K. et al. (1991) Circulation 83:356–362.
Mattson, F. et al. (1977) Journal of Nutrition 107:1139–1146.
Mattson, F. et al. (1976) Journal of Nutrition 106:747–752.
Codex Standard (1978) "Codex Standard for Process(ed) Cheese Preparations (process(ed) cheese food and process(ed) cheese spread)" Codex Standard A–8(c), pp. 1–3.
http://en.wikipedia.org/wiki/Codex_Alimentarius, "Codex Alimentarius", pp. 1–3, last visited May 12, 2006.
Food Standards Agency, United Kingdom "The condensed milk and dried milk regulations 2003".
Tholstrup, T. et al. (2004) Journal American College of Nutrition 23(2):169–176.
Denis, W. and S. Minot (1918) J. Biol. Chem. 36(11):59–67.
Farquhar, J. et al. (1956) Circulation 14:77–82.
Beveridge, J. et al. (1956) Canadian Journal of Biochemistry and Physiology 34:441–455.
The Merck Manual of Diagnosis and Therapy (Robert Berkow ed., Merk Sharp & Dohme Research Laboratories 1982) pp. 970–971.
Becker M., et al. (1993) Journal of Pediatrics 122(2) 292–296.
Sande, M. and G. Mandell "Antimicrobial Agents" in The Pharmacological Basis for Therapeutics, Goodman, Goldmen eds. (6 ed. 1980).
Coiro, V. et al. (1997) Clin. Ter. 148(1–2):15–22 Abstract Only.
Yosef, I. et al. (1992) Hepatology 15(3):438–445.
Yosef, I. et al. (1987) Hepatology 7(3):535–542.
Chowdhury, J. e tal. (1976) Experientia 32:1173–1175.
Peterson, D.W., Effect of Soybean Sterols in the Diet on Plasma and Liver Cholesterol in Chicks, Proceedings of the Society for Experimental Biology and Medicine, 1951, pp. 143–147, vol. 78, No. 1, USA.
Miller, Jonathan P., et al, Regression Studies with Safflower Oil and Sitosterol in Rabbit Atherosclerosis, Journal of the American Heart Association, 1959, pp. 779–786, vol. 7, American Heart Association, USA.
Beveridge, J.M.R., et al, Magnitude of the Hypocholesterolemic Effect of Dietary Sitosterol in Man, Journal of Nutrition, 1964, pp. 119–122, vol. 83, USA.
Mattson, Fred H., et al, Effect of Plant Sterol Esters on the Absorption of Dietary Cholesterol, Journal of Nutrition, 1976, pp. 1139–1146, USA.
O'Brien, Barbara C., Interrelated Effects of Food Lipids on Steroid Metabolism in Rats, Journal of Nutrition, 1977, pp. 1444–1454, vol. 107, USA.
Sugano, Michihiro, et al, A Comparison of Hypocholesterolemic Activity of Sitosterol and Sitostanol in Rats, Journal of Nutrition, 1977, pp. 2011–2019, vol. 107, USA.
Ikea and Sugano, Comparison of Absorption and Metabolism of Sitosterol and Sitostanol in Rats, Atherosclerosis, 1978, pp. 227–237, vol. 30, Elsevier/North–Holland Scientific Publishers, Ltd., USA.
Ikeda, Ikuo, et al, Inhitition of cholesterol absorption in rats by plant sterols, Journal of Lipid Research, 1988, pp. 1573–1582, vol. 29, USA.
Ikeda, Ikuo, et al, Effects of Sitosterol and Stiostanol on Micellar Solubility of Cholesterol, Journal of Nutritional Science and Vitaminology, 1989, pp. 361–369, vol. 35, Center for Academic Publications, Japan.
Peterson, D.W., Effect of Sterols on the Growth of Chicks Fed High Alfalfa Diets or a Diet Containing Quillaja Saponin, Journal of Nutrition, 1950, pp. 597–607, USA.
Mattson, Fred H., et al, The Effect of a Nonabsorbable Lipid, Sucrose Polyester, on the Absorption of Dietary Cholesterol by the Rat, Journal of Nutrition, 1976, pp. 747–752, vol. 106, USA.
Harper, A.E., Amino Acid Balance and Imbalance, Journal of Nutrition, 1958, pp. 405–418, USA.
Rogers and Harper, Amino Acid Diets and Maximal Growth in the Rat, Journal of Nutrition, 1965, pp. 267–273, vol. 87, USA.
Committee of the Council of American Institute of Nutrition, Report of the American Institute of Nutrition Ad Hoc Committee on Standards for Nutritional Studies, Journal of Nutrition, pp. 1340–1348, USA.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-14 are cancelled.

* * * * *